United States Patent [19]

Majewski et al.

[11] Patent Number: 5,742,660
[45] Date of Patent: Apr. 21, 1998

[54] DUAL ENERGY SCANNING BEAM LAMINOGRAPHIC X-RADIOGRAPHY

[75] Inventors: Stanislaw Majewski, Grafton; Randolph F. Wojcik, Yorktown, both of Va.

[73] Assignee: Southeastern Universities Research Association, Inc., Newport News, Va.

[21] Appl. No.: 781,722

[22] Filed: Jan. 10, 1997

[51] Int. Cl.⁶ .................................................. H05G 1/64
[52] U.S. Cl. .................................. 378/98.9; 378/146
[58] Field of Search .................................. 378/98.9, 98.8, 378/46, 51, 19, 156, 185, 175, 146

[56] References Cited

U.S. PATENT DOCUMENTS

| | | | |
|---|---|---|---|
| 4,972,900 | 11/1990 | Sones et al. | 378/98.9 |
| 4,979,201 | 12/1990 | Kruger | 378/175 |

*Primary Examiner*—Don Wong

[57] ABSTRACT

A multiple x-ray energy level imaging system includes a scanning x-ray beam and two detector design having a first low x-ray energy sensitive detector and a second high x-ray energy sensitive detector. The low x-ray energy detector is placed next to or in front of the high x-ray energy detector. The low energy sensitive detector has small stopping power for x-rays. The lower energy x-rays are absorbed and converted into electrical signals while the majority of the higher energy x-rays pass through undetected. The high energy sensitive detector has a large stopping power for x-rays as well as it having a filter placed between it and the object to absorb the lower energy x-rays. In a second embodiment; a single energy sensitive detector is provided which provides an output signal proportional to the amount of energy in each individual x-ray it absorbed. It can then have an electronic threshold or thresholds set to select two or more energy ranges for the images. By having multiple detectors located at different positions, a dual energy laminography system is possible.

20 Claims, 2 Drawing Sheets

DUAL ENERGY SCANNING BEAM LAMINOGRAPHIC X-RADIOGRAPHY

GOVERNMENT RIGHTS

The United States may have certain rights to this invention under management and operating Contract DE-AC05-84 ER 40150 from the United States Department of Energy.

BACKGROUND OF THE INVENTION

1. Field of the Invention

The present invention pertains to x-radiology systems and more particularly to dual energy x-radiography in which images having multiple densities present can be distinguished.

2. Related Prior Art

Most x-radiography systems in use today measure the bulk x-ray transmission of an object in order to produce an image. In this approach, an object is situated in front of a photographic medium. X-radiation is generated and directed toward the object. A portion of the incident x-rays are absorbed by the object. The remainder of the x-rays pass through the object and expose the photographic medium. The problem with this approach is that a low density thick object looks the same as a high density thin object in the image. Thus, in an image with both types of objects, the images can not be distinguished to identify the specific features present. Also, if the features of a low-Z material in the presence of an overlying high-Z material are to be determined, the high-Z material can partially hide these features. A method used to overcome these problems is computed tomography (CT) which takes images from many hundreds of different angles. This technique, however, suffers from "beam hardening" which means that the lower energy x-rays are absorbed easier than the higher energy x-rays, which causes artifacts in the image. Again, this problem is due to the fact that only the bulk x-ray transmission is measured. X-rays with an energy less than two hundred keV interact with matter primarily only through photoelectric and Compton interactions. A photoelectric type of interactions are dominated by the Z of the material while Compton type of interactions are dominated by the electron density of the material. By separately measuring high energy x-rays vs. low energy x-rays, the photoelectric vs. Compton interactions can be reconstructively measured, which are dependent on the type of material and not its thickness. The image can be reconstructed as if it had been taken with mono-energetic x-rays.

In the past, dual energy x-radiography has been attempted in many ways. In one method, two images of an object are taken, one at a low keV setting on the x-ray tube and one at a high keV setting on the x-ray tube. In this method a bulk x-ray imaging system is used. Movement of the object between images can cause problems in the reconstruction. Also, the high keV setting produces a significant number of low energy x-rays thus reducing the ability of effectively separating the types of interactions.

A second method uses two detectors, one detector sensitive to low energy x-rays in front of another detector that is sensitive to high energy x-rays. The high-low x-ray energy sensitivity is mechanically built into the detector and can not be changed without mechanical modifications. This detector, or array of such detectors, is mechanically scanned over the object. Mechanical scanning is a relatively slow process and can take many seconds to minutes even for a low resolution image. The larger the array, the faster the image acquisition, however, the amount of readout electronics increases rapidly as does the cost of the system. Also, very high resolutions require the size of the detectors to be on the order of a few hundred microns which require expensive microelectronics technology.

A third method which has been attempted is to use energy sensitive detectors which actually measure the energy of the incoming x-ray. The problem with such detectors is that they can not handle very high rates and thus, it takes longer to acquire an image. To increase the speed of acquisition, an array of detectors as large as the object is needed with many thousands of electronic channels. The advantage of such a system is that the detectors can be electronically tuned to select the cutoff between the high versus low energy x-ray detection.

Scanning x-ray beam radiography has also been developed, most notably the Reverse Geometry X-radiography system. In this system, the x-ray beam is rastered across an object and one or more detectors are used to obtain an image. These detectors, however, only measure the bulk x-ray transmission of the object. Consequently, this system suffers from the same problems noted in the methods noted above. Using several of these detectors a Laminography system can be obtained. This Laminography system is basically a low resolution CT or computed tomography system.

Dual energy has also been used in computed tomography systems, however, to obtain a high resolution system, detectors of a few microns and a great deal of readout electronics to handle the detector output are required. These systems also require a significant amount of time totaling several minutes to acquire an image. This occurs since the detector must be rotated around the object as well as moved up and down the object for a three dimensional image.

Examples of related art methods and apparatus that are used in obtaining sophisticated x-ray images are illustrated in the following United States patents.

U.S. Pat. No. 4,864,594, titled "Bone Mineral Density Measurement", issued to Dan Inbar et al., relates to an in-vivo bone measuring system using a modified emission computed tomographic gamma camera arrangement. This arrangement is used for detecting radiation from two separate sources located outside of the body of the patient. The two separate sources are oppositely disposed to the gamma camera during rotation of the gamma camera and the radiation sources about the patient for obtaining tomographic data. The two separate sources emit at least two different energy levels. The system includes a processing system for processing the detected radiation to provide a bone mineral density map.

U.S. Pat. No. 5,020,085, titled "X-ray Image Processing Device", issued to Toshiyuki Kawara et al., relates to an x-ray image processing device that uses a dual energy projection radiography method. In this method the low energy image and the high energy image are subjected to a subtraction process to provide a first image such as a conventional bone x-ray image. The first image, similar to a conventional bone x-ray, and the low energy image are subjected to a second subtraction process to produce a second image. The second image is similar to a soft tissue x-ray image. This two step process is alleged to be capable of its image production without deterioration of the x-ray image.

U.S. Pat. No. 5,402,460, titled "Three-Dimensional Microtomographic Analysis System", issued to Roger H. Johnson et al., relates to a microtomographic system that is used to generate a three dimensional image of a specimen. The microtomographic system includes an x-ray generator that produces an x-ray beam, a specimen holder that holds the specimen in the beam and an x-ray detector that measures the attenuation of the beam through the specimen. Two projections of each view of the specimen are made. Each projection is made with a different intensity x-ray beam. After a set of projections of one view of the specimen is made, the specimen is rotated on the specimen holder and another set of projections is made. The projections of each view of the specimen are analyzed together to provide a quantitative indication of the phase fraction of the material comprising the specimen. The projections of the different views are combined to provide a three dimensional image of the specimen.

SUMMARY OF THE INVENTION

The present invention provides a method of operation in which an x-ray image is obtained by raster scanning an x-ray beam over an object. An energy discriminating detector is situated so that it absorbs the x-rays that have passed through the object. The energy discriminating detector of the present invention can be of two types. The first embodiment of the energy discriminating detector of present invention is a two detector design made up of a low x-ray energy sensitive detector placed next to or in front of a high x-ray energy sensitive detector. The low x-ray energy sensitive detector is made so by virtue of its small stopping power for x-rays. The lower energy x-rays are absorbed and converted into electrical signals while the majority of the higher energy x-rays pass through undetected. The high energy sensitive detector is made so by virtue of it having a large stopping power for x-rays as well as it having a filter placed between it and the object to absorb the lower energy x-rays.

In the second embodiment of the energy discriminating detector of the present invention, a single energy sensitive detector is used which provides an output signal proportional to the amount of energy in each individual x-ray it absorbed. It can then have an electronic threshold or thresholds set to select two or more energy ranges for the images.

By having a few tens of these detectors located at different positions, a dual energy laminography system can be achieved. With multiple detectors located at different positions, an accurate three dimensional image of an object having multiple densities can be obtained.

DESCRIPTION OF THE PREFERRED EMBODIMENT

Figure 1:
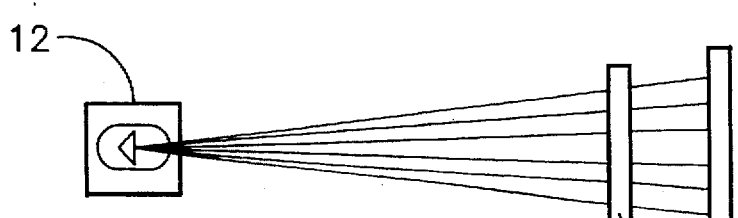
FIG. 1 is a partial block diagram of a co x-radiography imaging system.

In standard x-radiography, only a two dimensional shadow outline of an object is obtained. Differentiation between a thick low stopping power object and a thin high stopping power object can not be obtained. A partial block diagram of a conventional x-radiography imaging system is illustrated in FIG. 1. In a conventional x-radiography system, an x-ray point source 12 is used to generate x-rays to be incident upon an object 14. A photographic film 16 is placed behind object 14. Film 16 acts as a detector, being exposed by x-rays that are not absorbed by object 14. As indicated previously, the Z of the object cannot be differentiated and the photographic image is the same whether the object is thick object having a low stopping power or low absorption ability for x-rays, or a thin object having a high stopping power or high absorption ability for x-rays.

Figure 2:
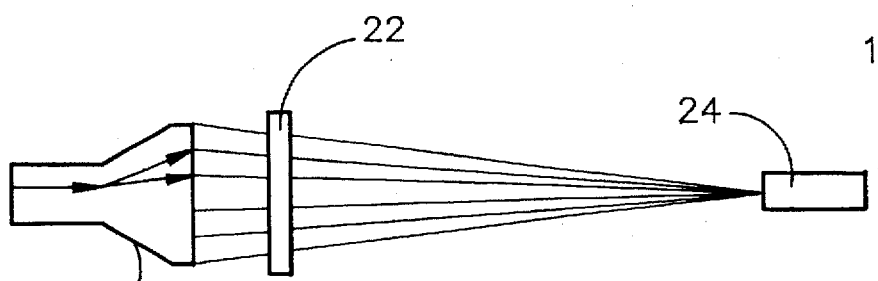
FIG. 2 is a partial block diagram of an x-radiography imaging system in which the present invention may be utilized.

FIG. 2 illustrates a x-radiography system of the type for use with the present invention. A raster scanning x-ray tube 20 is used instead of a point source. An object 22 is placed next to or in juxtaposition with scanning x-ray 20 so that the x-rays generated by tube 20 are incident upon object 22. Some x-rays are absorbed by object 22 and others travel to and are focused on point detector 24. In this system; an advantage is obtained by using a point detector. Scattered x-rays and other non-focused x-rays that may blur or cloud the image of object 22 are not detected. Only focused x-rays are detected and contribute to the image produced by detector. Detector 24 may be as simple as being composed of a scintillator and a photomultiplier tube (PMT), which measures the intensity of the transmitted x-ray flux. The signal produced by the detector is digitized by a sampling twelve bit analog to digital convertor and correlated to the location of the x-ray spot to build up a two dimensional image. By using this system, it is possible to shrink the raster pattern and achieve linear magnification of up to twenty-five times. The raster pattern can also be electronically panned over the face of the tube to look at different areas. Due to its high scanning rate and its ability to read two point detectors at the same time, stereoscopic x-ray images can be obtained.

Figure 3:
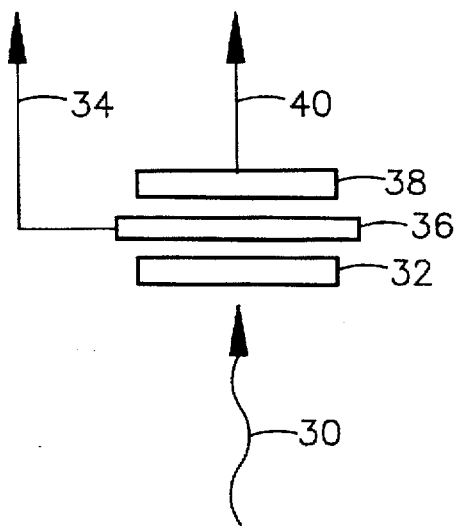
FIG. 3 is a partial block diagram of a first embodiment of a dual energy x-radiography imaging system.

Referring now to FIG. 3, a block diagram of a first embodiment of the present invention is illustrated. Incoming x-rays 30 are incident upon low x-ray energy sensitive detector 32. The signal produced through x-ray energy absorption by low x-ray energy detector 32 is transmitted to a display (not shown) via low energy image connection 34. High energy x-rays pass through detector 32 and are incident upon energy separation filter 36 if required. Filter 36 is required only if detector 32 is incapable of absorbing most of the low energy x-rays. Behind filter 36 is located a high x-ray energy sensitive detector 38 which receives all x-radiation that has not been absorbed by either low x-ray energy sensitive detector 32 or filter 36. Low x-ray energy sensitive detector 38 provides signals relating to a high energy image via high energy image connection 40. The signals provided by low x-ray energy sensitive detector 32 and high x-ray energy sensitive detector 38 may be provided to any current display in use in the arts such as a cathode ray tube, etc.

In the preferred embodiments low x-ray energy sensitive detector 32 is preferably made of a three hundred micrometer thick piece of Yttrium aluminum perovskite (YAP). However, any suitable material known in the art for absorbing low energy x-rays may be used. Filter 36 is preferably a 0.38 mm copper filter to enhance the low vs. high energy separation. Any type of filter may be used as long as it is capable of effecting the low vs. high energy separation. High x-ray energy sensitive detector 38 is preferably a one centimeter thick piece of lutetium oxyorthosilicate (LSO), although, as with the low energy x-ray detector, any suitable type of detector for absorbing high energy x-rays Currently available in the art may be used.

Figure 4:
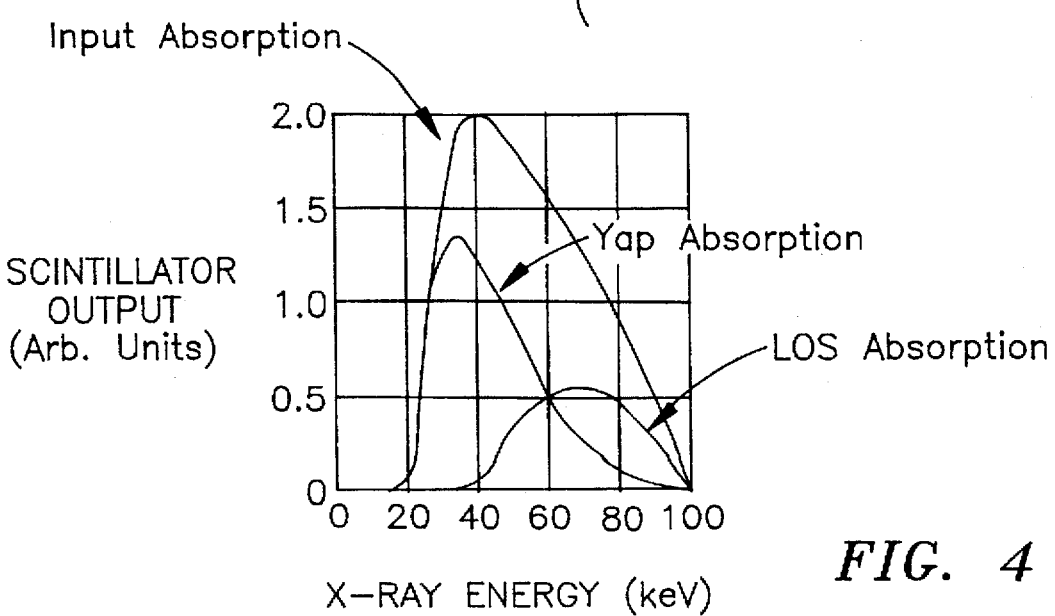
FIG. 4 of a graph illustrating the x-ray absorptions of the dual energy detector of FIG. 3.

FIG. 4 of a graph illustrating the x-ray absorption characteristics of the crystalline materials used in the dual energy detector of FIG. 3. In order to determine the required thicknesses of the absorption crystals used as low x-ray energy sensitive detector 32, Yttrium aluminum perovskite, and high x-ray energy sensitive detector 38, lutetium oxyorthosilicate, a simulation was made using Photocoef. This simulation was performed to analyze the various x-ray absorption of the substances used in the preferred embodiment. A simple bremsstrahlung spectrum filtered by two millimeter aluminum was assumed as an input spectrum and is shown as curve A. This assumption was made without taking tungsten's characteristic lines into account. In the preferred embodiment, the scanning x-ray plate emits x-rays produced by a microfocused beam of up to one hundred keV electrons striking a tungsten target or window anode. In this type of system the input spectrum will have characteristic wavelength bands from tungsten in the input spectrum, but for this application, the bands will not significantly affect the outcome. The yttrium aluminum perovskite (YAP) absorption peaks around thirty-five keV as shown by curve B. The lutetium oxyorthosilicate (LSO), with copper filter 36, peaks around seventy keV as shown by curve C. In a dual energy imaging system, the main factors affecting image quality are the energy separation and the detected photon fluences. A separation of thirty-five keV is quite good.

Figure 5:
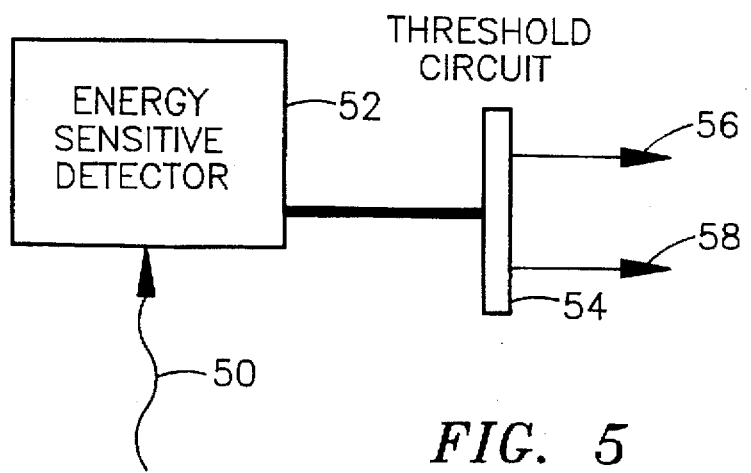
FIG. 5 is a partial block diagram of a second embodiment of a dual energy x-radiography imaging system.

In FIG. 5 a partial block diagram of a second embodiment of a dual energy x-radiography imaging system is illustrated as having incoming x-rays 50 incident upon an x-ray energy sensitive detector 52. X-ray energy sensitive detector 52 is connected to a threshold circuit 54. Threshold circuit 54 provides two outputs, one relating to a low energy image at output 56 and one relating to a high energy image at output 58.

In this embodiment, a single dual sensitive detector is used that is capable of detecting two or more x-ray energy levels at the same time. It produces one signal in response to the absorption of low energy x-rays and a second signal in response to absorption of high energy x-rays. These two images are formed separately and combined to produce a single image. Combining the two images is possible since the images are obtained simultaneously.

Figure 6:
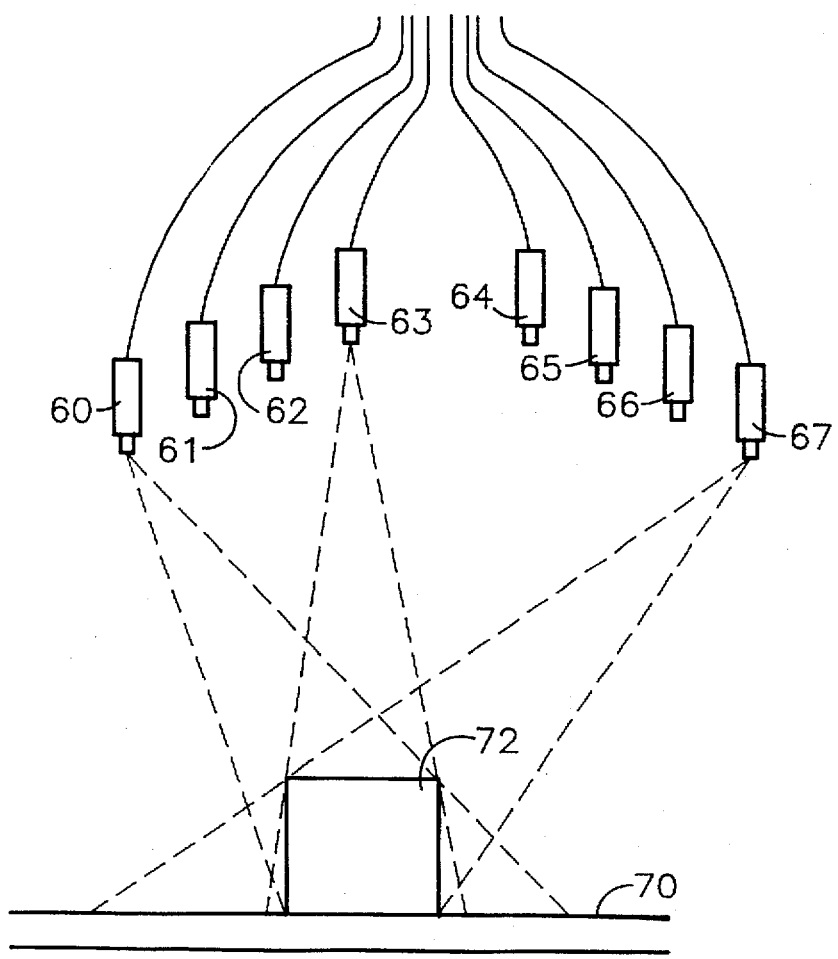
FIG. 6 is a partial block diagram of a laminographic multiple energy sensitive detector system.

Referring now to FIG. 6 a partial block diagram of a laminographic multiple energy sensitive detector system is illustrated. Multiple detectors 60–67 are spaced apart along an area 68, each detector having a different view of the object of which an image is to be taken. Scanning x-ray plate 70 emits x-rays produced by a microfocused beam of up to one hundred keV electrons striking a tungsten target or window anode. Magnetic deflection coils are used to sweep the electron beam in a raster pattern across the broad anode plate producing a moving point x-ray source. The x-rays are emitted in a range under two hundred keV. The x-rays pass through object 72 and are incident upon detectors 60–67. By determining the amount of x-rays absorbed, an image of the object and its density or densities can be determined as previously explained. Because of the positioning of detectors 60–67 a three dimensional image may be obtained. Detector 60 views object 72 from a totally different view than detector 67. The image received by detector 61 provides a slightly different view than that obtained by detector 60. In a similar manner, the image received by detector 62 is slightly different than that received by detector 61. Each of the detectors 60–67 receives a slightly different image, at a slightly different angle and containing more of one side or the other side, than each of the other detectors. In this manner, a three dimensional image can be created from the individual images provided by each of detectors 60–67. With the dual energy capability of the detectors, a three dimensional, density identified image can be made which accurately approximates the appearance of the object under analysis.

Combining a scanning x-ray beam with either of the two embodiments of the present invention produces an inexpensive, simple and fast dual energy x-ray imaging system. Since the speed of acquisition is defined by how fast the x-rays can be rastered over the object, which is much faster than any mechanical scanning, speed is greatly improved. Also, since the resolution is defined by how the x-ray source is rastered, the size of the detectors has little impact on the resolution and no impact on the speed. Using an array of a few hundred small energy sensitive detectors (as compared to a few thousand above) an image can be acquired at about the same speed as before but with a factor of ten decrease in complexity and cost. When used with multiple detectors at various positions, a three dimensional image can be obtained without image artifacts again with reduced complexity and cost over a standard CT system.

The apparatus and method of the present invention includes the ability to use relatively large size inexpensive energy sensitive detectors to produce high resolution dual energy laminographic images. The scanning x-ray beam technique allows one to obtain dual energy images much faster than with mechanical scanning used in conventional dual energy radiography. The simplicity of the dual energy detector system of the apparatus of the present invention allows reduced complexity and cost as compared to conventional dual energy x-radiography or CT.

While there has been illustrated and described particular embodiments of the present invention, it will be appreciated that numerous changes and modifications will occur to those skilled in the art, and it is intended in the appended claims to cover all those changes and modifications which fall within the true spirit and scope of the present invention.

We claim:

1. A multiple x-ray energy level imaging system comprising:

apparatus for providing a raster pattern scanning x-ray tube beam; and a single point detector apparatus for detecting at least two different energy level x-rays as said raster pattern is scanned.

2. The multiple x-ray energy level imaging system according to claim 1 wherein said single point detector apparatus for detecting includes:

a first low x-ray energy sensitive single point detector; and a second high x-ray energy sensitive single point detector placed near said low x-ray energy single point detector.

3. The multiple x-ray energy level imaging system according to claim 2 wherein said first low energy sensitive single point detector has small stopping power for x-rays.

4. The multiple x-ray energy level imaging system according to claim 3 wherein said first low energy sensitive single point detector absorbs and converts the lower energy x-rays into electrical signals while the majority of the higher energy x-rays pass through undetected.

5. The multiple x-ray energy level imaging system according to claim 2 wherein said second high energy sensitive single point detector has a large stopping power for x-rays.

6. The multiple x-ray energy level imaging system according to claim 5 wherein said second high energy sensitive single point absorbs and converts the high energy x-rays into electrical signals.

7. The multiple x-ray energy level imaging system according to claim 2 also including a filter placed between said first low x-ray energy sensitive single point detector said second high x-ray energy sensitive single point detector to absorb the lower energy x-rays.

8. The multiple x-ray energy level imaging system according to claim 1 wherein said single point detector apparatus for detecting includes:

an energy sensitive single point detector which provides an output signal proportional to the amount of energy in each individual x-ray detected.

9. A method for imaging multiple x-ray energy levels comprising:

raster pattern scanning an object with an x-ray beam emanating from a raster scanned source of x-rays and detecting using a single point detector apparatus at least two different energy level x-rays as said raster pattern is scanned.

10. The method for imaging multiple x-ray energy levels according to claim 9 wherein said detecting includes:

distinguishing a first low x-ray energy level with a low x-ray energy single point detector; and distinguishing a second high x-ray energy level with a high x-ray energy single point detector placed near said low x-ray energy single point detector.

11. The method for imaging multiple x-ray energy levels according to claim 10 wherein distinguishing a first low energy level includes stopping low energy x-rays.

12. The method for imaging multiple x-ray energy levels according to claim 11 wherein said stopping low energy x-rays includes:

absorbing lower energy x-rays;

converting lower energy x-rays into electrical signals; and passing higher energy x-rays.

13. The method for imaging multiple x-ray energy levels according to claim 10 wherein said distinguishing a second high x-ray energy level includes stopping high energy x-rays.

14. The method for imaging multiple x-ray energy levels according to claim 10 also includes:

providing a filter between said low x-ray energy single point detector and said high x-ray energy single point detector; and absorbing lower energy x-rays in said filter.

15. The method for imaging multiple x-ray energy levels according to claim 14 wherein said stopping high energy x-rays includes:

absorbing high energy x-rays; and converting high energy x-rays into electrical signals.

16. The method for imaging multiple x-ray energy levels according to claim 9 wherein said detecting includes:

providing an output signal proportional to the amount of energy in each individual x-ray detected.

17. A multiple x-ray energy level imaging system for providing an image of an object having a plurality of densities comprising:

apparatus for providing a raster pattern scanning x-ray beam having multiple energy levels; and a single point detector apparatus for detecting at least two different energy level x-rays and absorbing said different energy level x-rays and converting each of said absorbed different energy level x-rays into electrical signals representative of the intensity of said different energy level x-rays.

18. The multiple x-ray energy level imaging system according to claim 17 wherein said single point detector apparatus for detecting includes a plurality of spaced apart single point detector apparatus, each having:

a first low x-ray energy sensitive single point detector; and a second high x-ray energy sensitive single point detector placed near said low x-ray energy detector.

19. The multiple x-ray energy level imaging system according to claim 18 also including a filter placed between each said first low x-ray energy sensitive single point detector and said second high x-ray energy sensitive single point detector to absorb lower energy x-rays.

20. The multiple x-ray energy level imaging system according to claim 17 wherein said single point detector apparatus for detecting includes:

a plurality of energy sensitive single point detectors spaced apart in an area near an object which provide output signals proportional to the amount of energy of each individual x-ray detected passing through said object.

* * * * *